(12) United States Patent
Galimi et al.

(10) Patent No.: US 8,389,722 B2
(45) Date of Patent: Mar. 5, 2013

(54) ADEFOVIR DIPIVOXIL CRYSTALLINE MONOHYDRATE FORM

(75) Inventors: Stefania Galimi, Garbagnate M. SE (IT); Emilio Vecchio, Garbagnate M. SE (IT); Roberta Pizzocaro, Garbagnate M. SE (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 304 days.

(21) Appl. No.: 12/671,556

(22) PCT Filed: Jul. 31, 2008

(86) PCT No.: PCT/EP2008/006320
§ 371 (c)(1), (2), (4) Date: Apr. 1, 2010

(87) PCT Pub. No.: WO2009/015892
PCT Pub. Date: Feb. 5, 2009

(65) Prior Publication Data
US 2010/0292470 A1  Nov. 18, 2010

(30) Foreign Application Priority Data

Aug. 2, 2007  (IT) .............................. MI2007A1594

(51) Int. Cl.
*C07F 9/6561* (2006.01)
*A61K 31/675* (2006.01)

(52) U.S. Cl. ...................................................... 544/244
(58) Field of Classification Search .................. 544/244
See application file for complete search history.

(56) References Cited

U.S. PATENT DOCUMENTS

2009/0247749 A1* 10/2009 Blazecka et al. ............. 544/277
2011/0207928 A1*  8/2011 Cho et al. ...................... 544/244
2012/0101273 A1*  4/2012 Choi et al. .................... 544/244

FOREIGN PATENT DOCUMENTS

CN         1935818 A  *  3/2007
WO   WO 9904774 A2  *  2/1999
WO         00/35460 A     6/2000

OTHER PUBLICATIONS

"Adefovir Dipivoxil Monohydrate (Antiviral)" (Apr. 2010) <http://www.solmag-olon.it/upload/19/ADEFOVIR_apr10.pdf> dowloaded from the internet May 9, 2012.*

* cited by examiner

*Primary Examiner* — Mark Berch
(74) *Attorney, Agent, or Firm* — Rothwell, Figg, Ernst & Manbeck, P.C.

(57) ABSTRACT

Adefovir Dipivoxil monohydrate crystalline is disclosed.

4 Claims, 12 Drawing Sheets

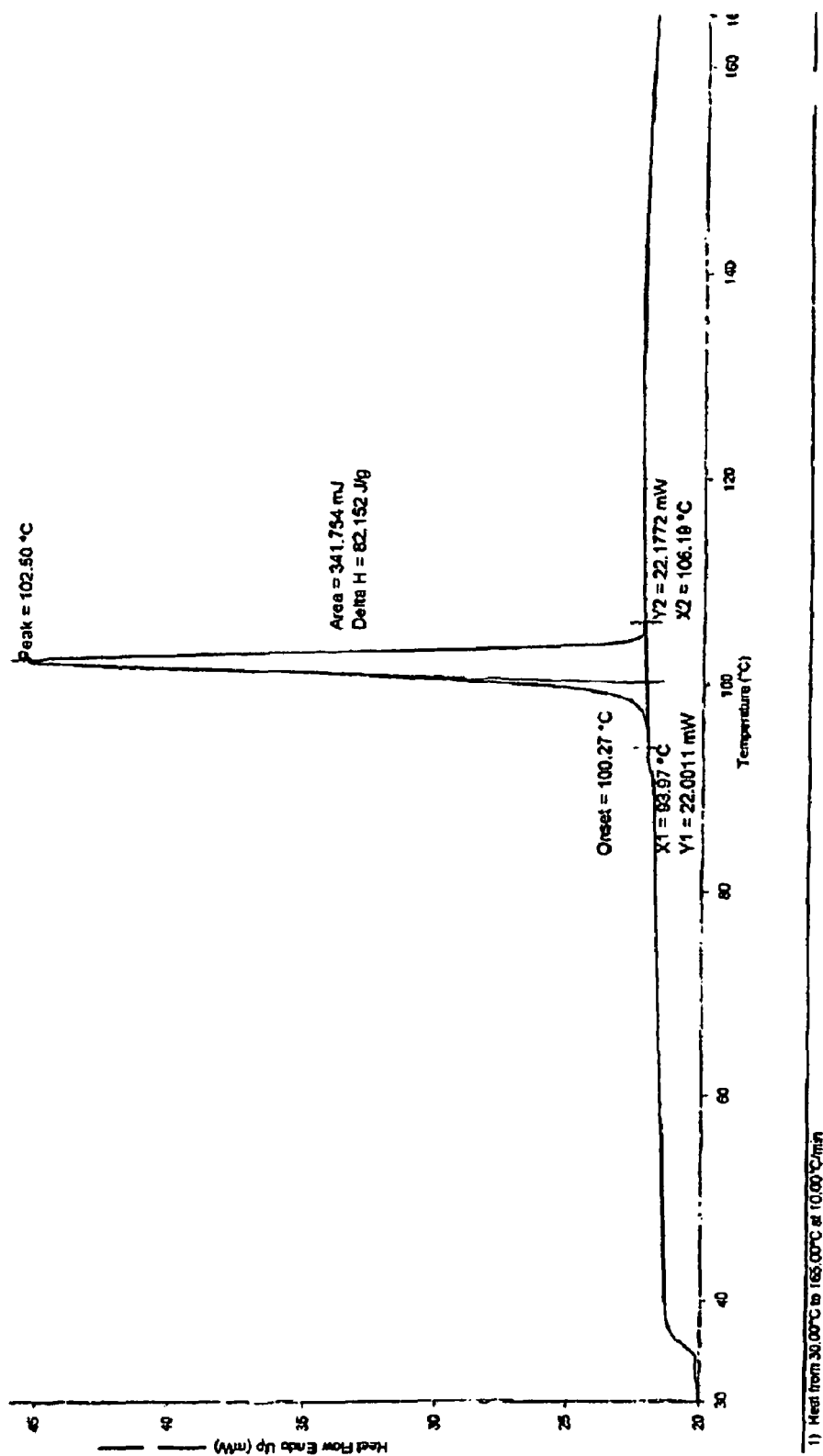
Figure 1 - DSC

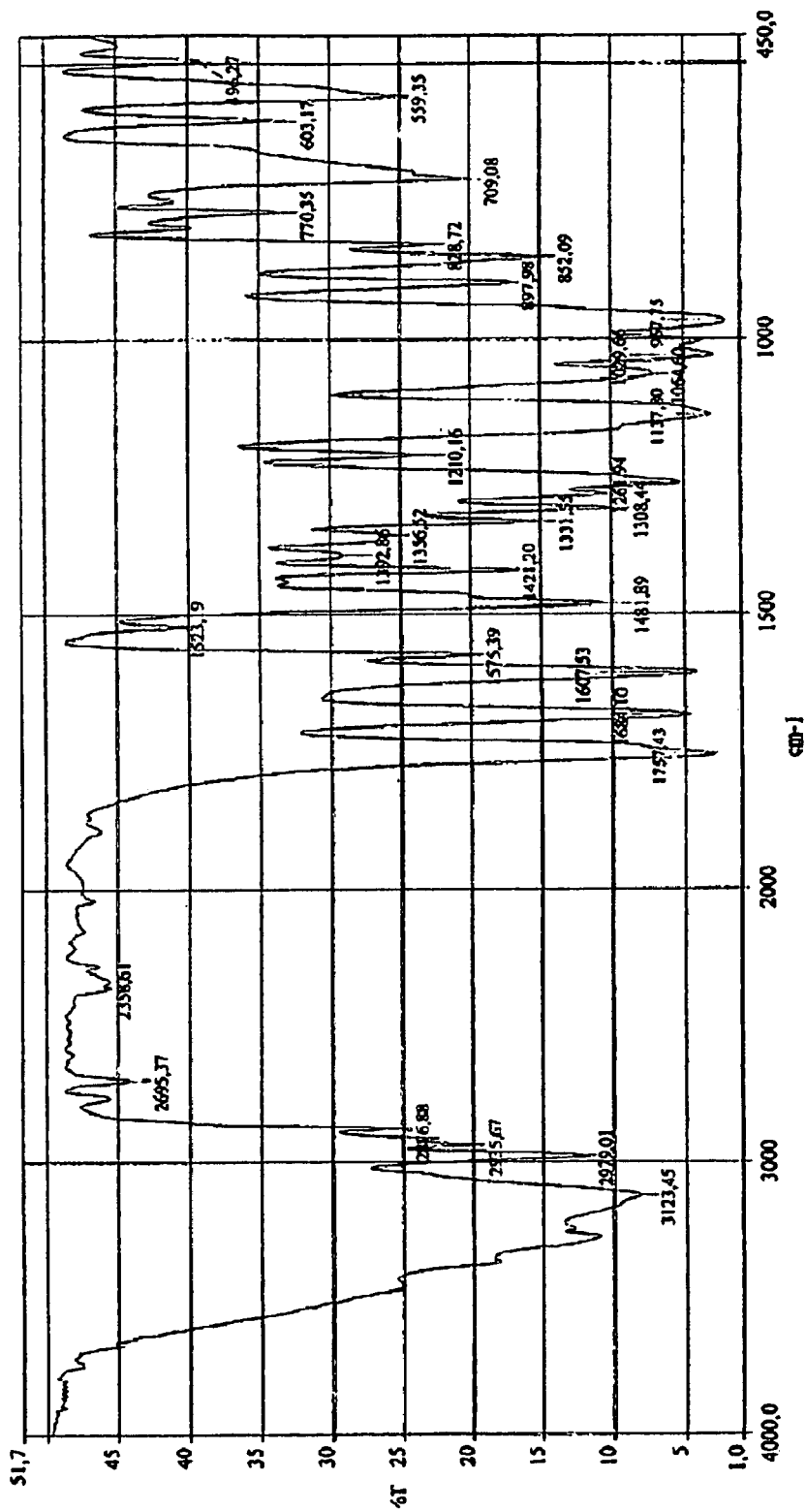
Figure 2 - IR

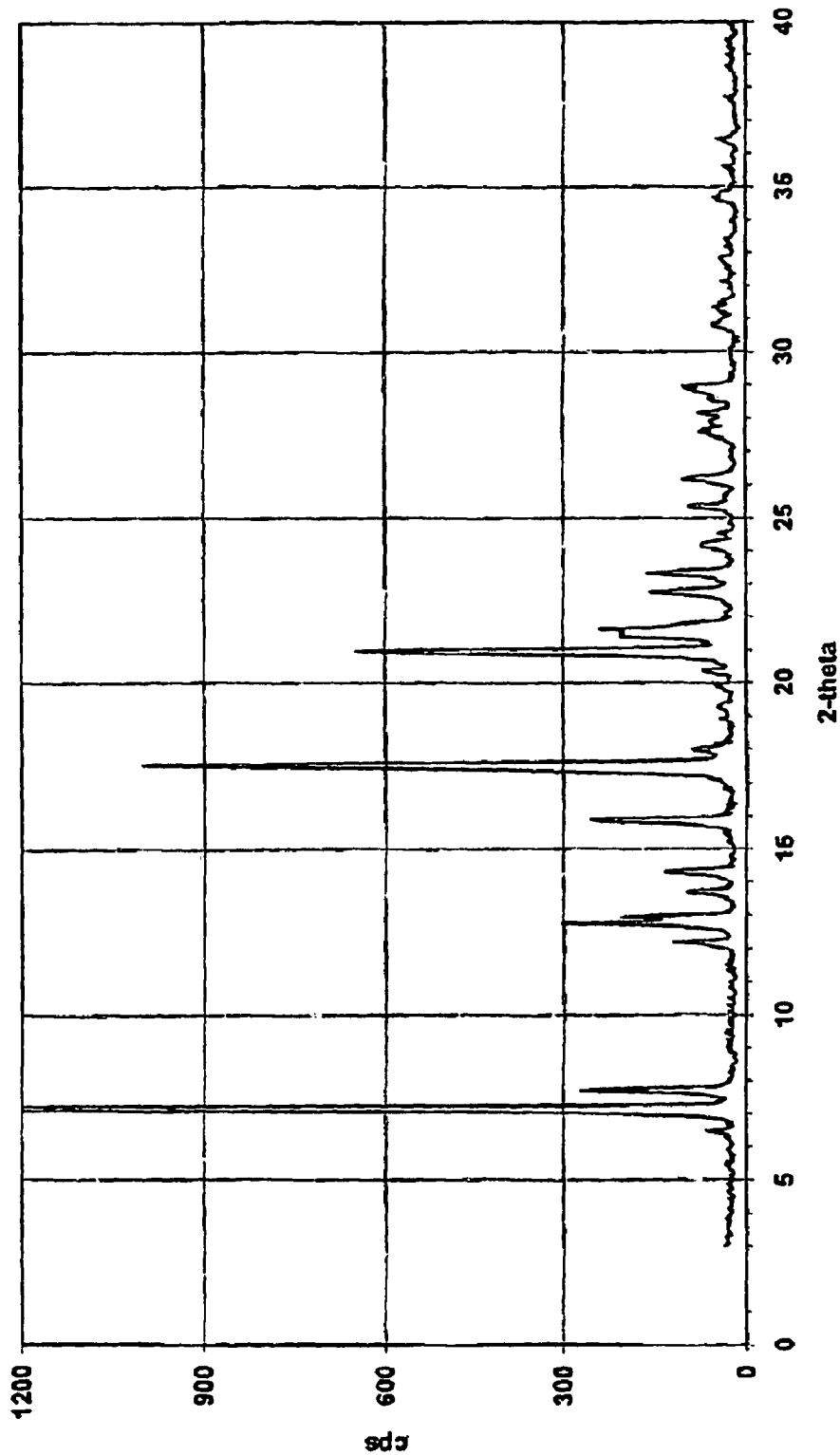
Figure 3 - x ray

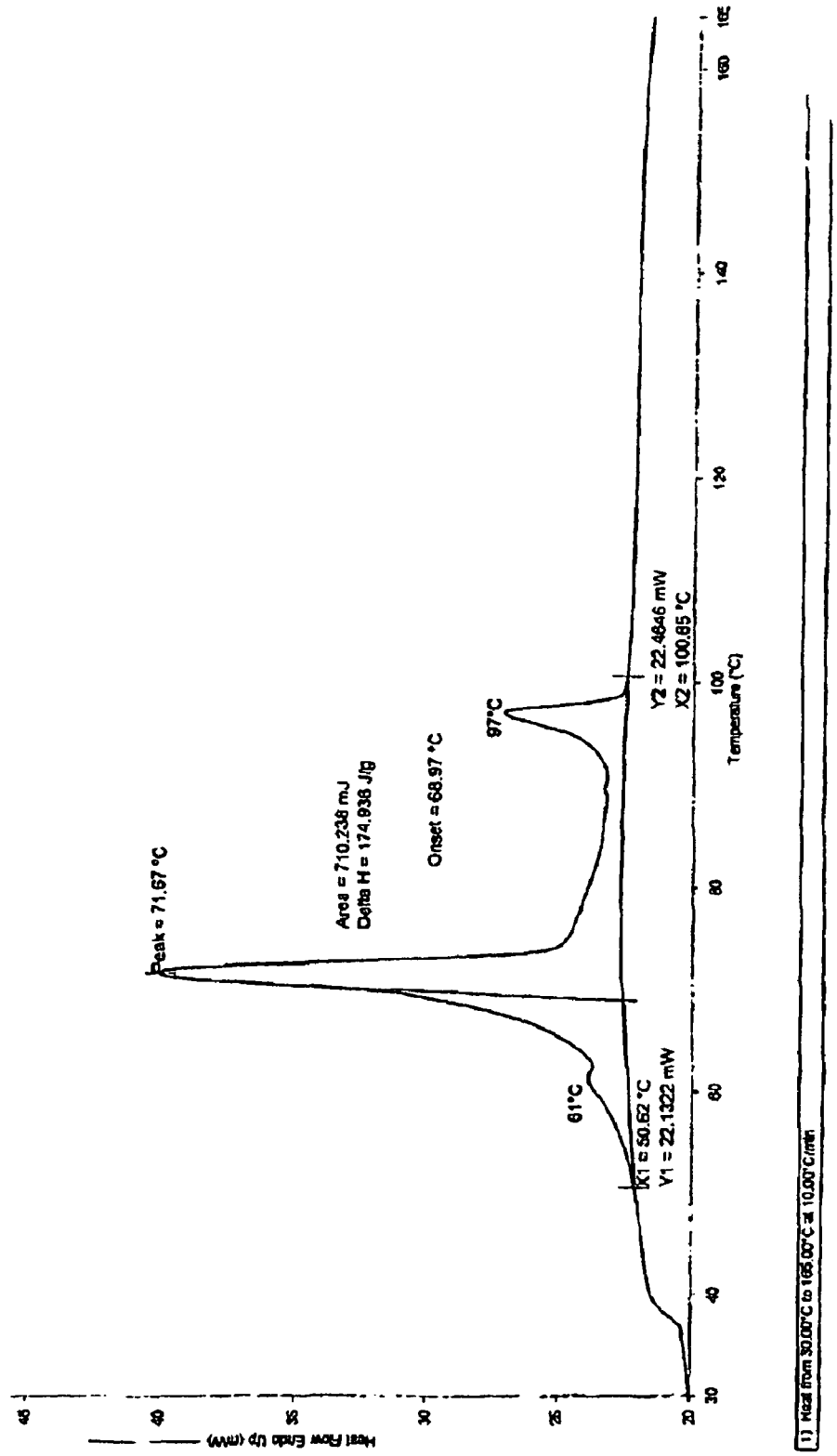
Figure 4 - DSC

Form 2 - Dihydrate
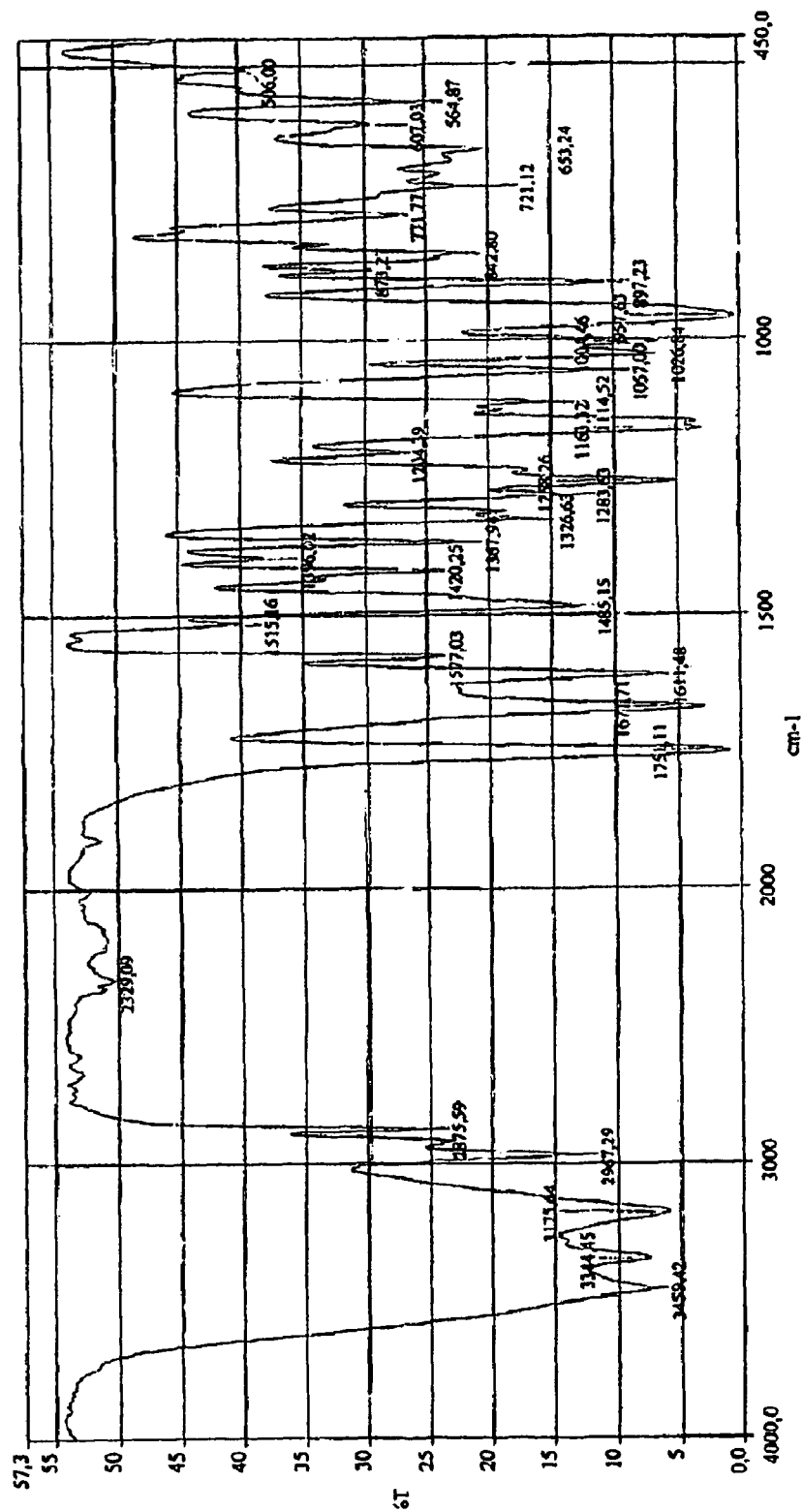
Figure 5 - IR

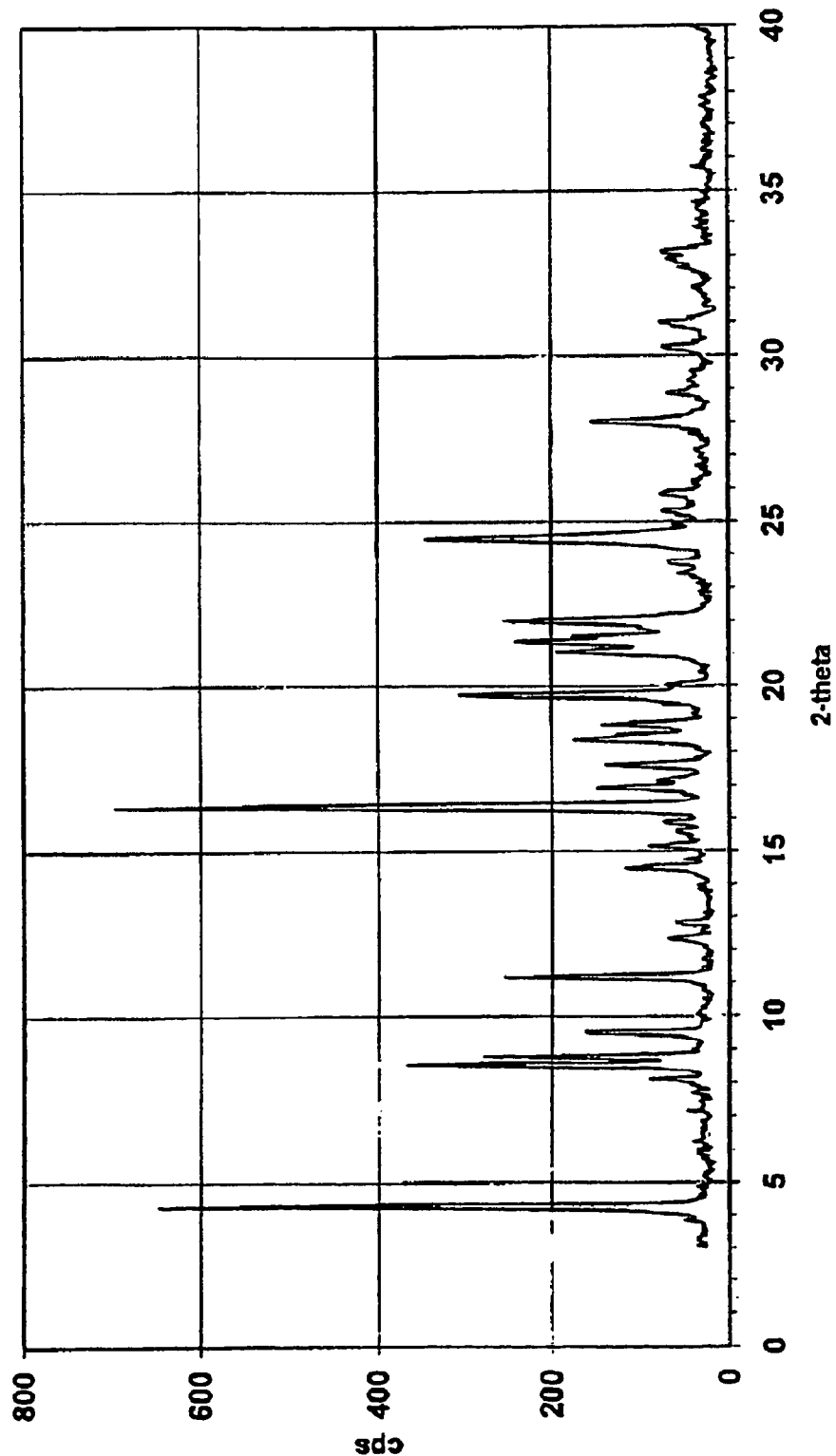
Figure 6 - x ray

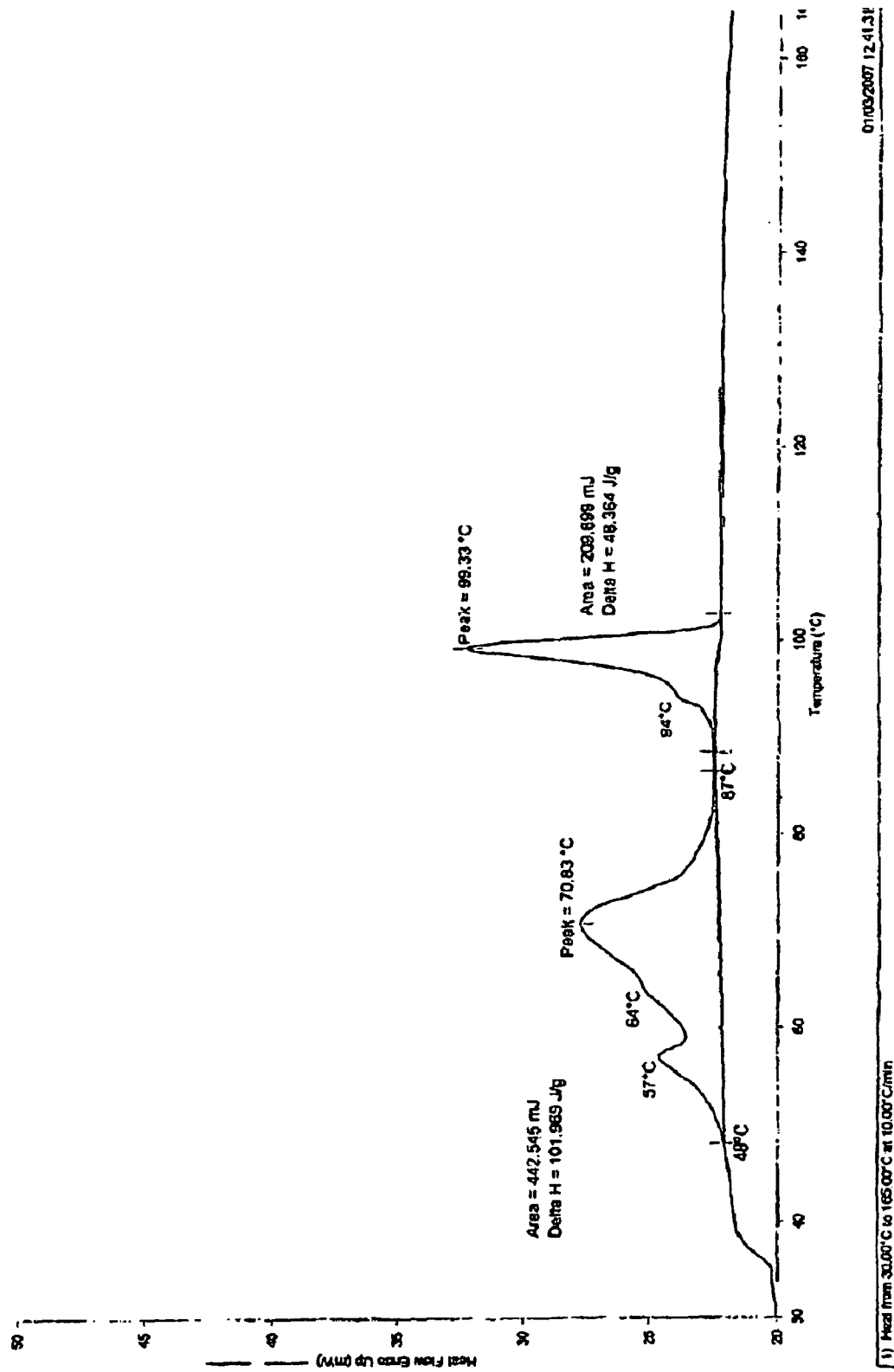
Figure 7 - DCS

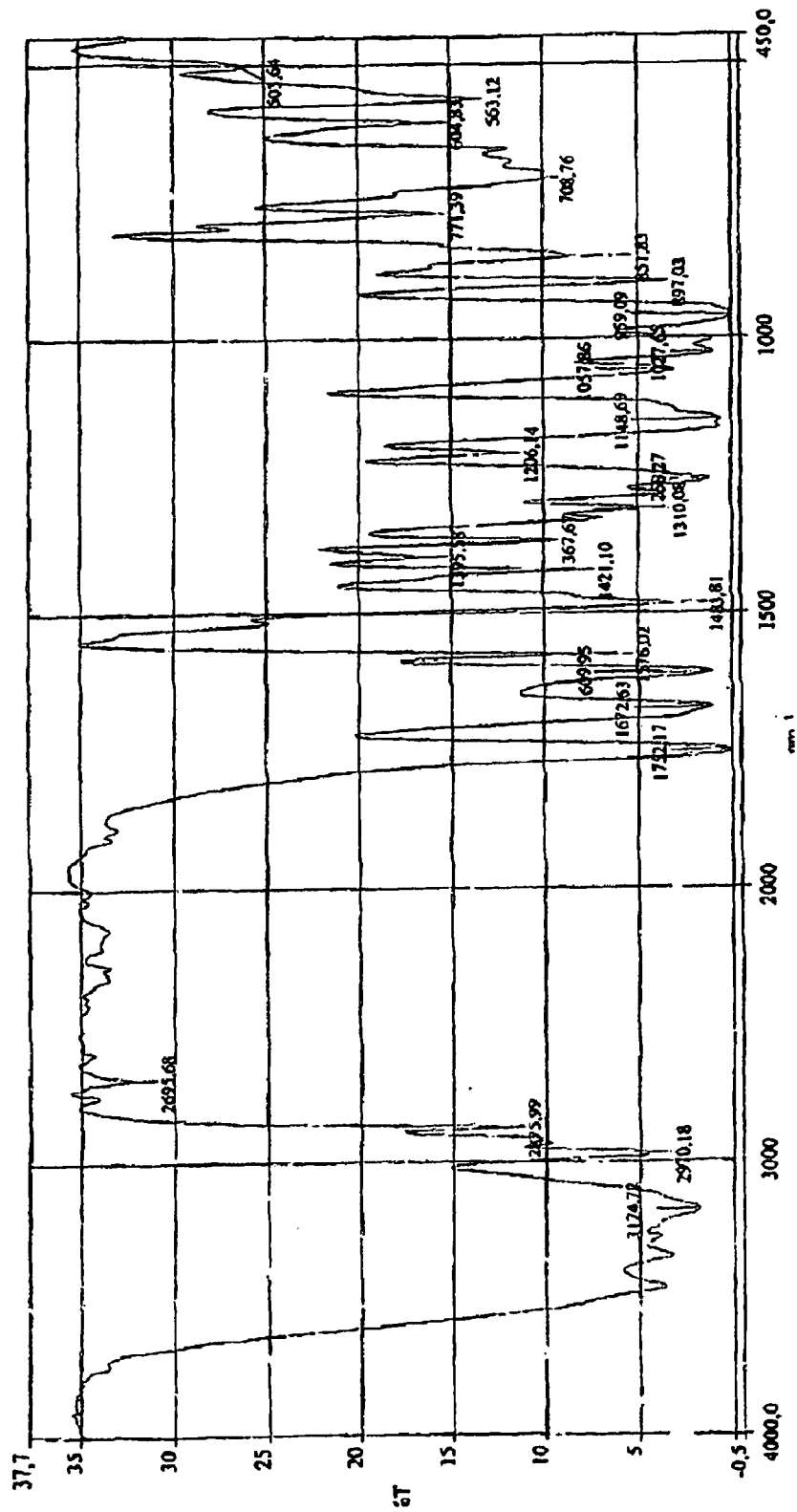
Figure 8 - IR

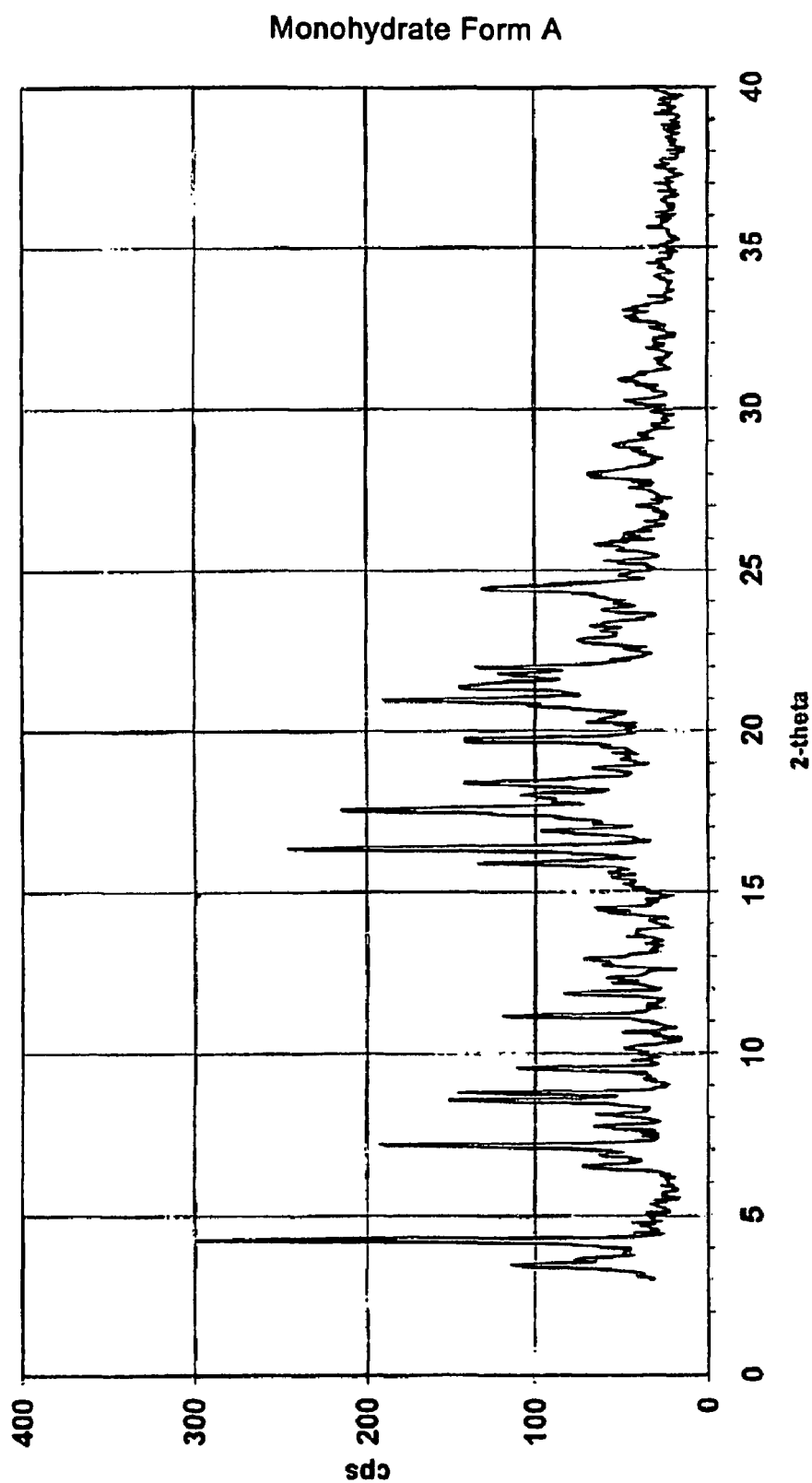
Figure 9 - x ray

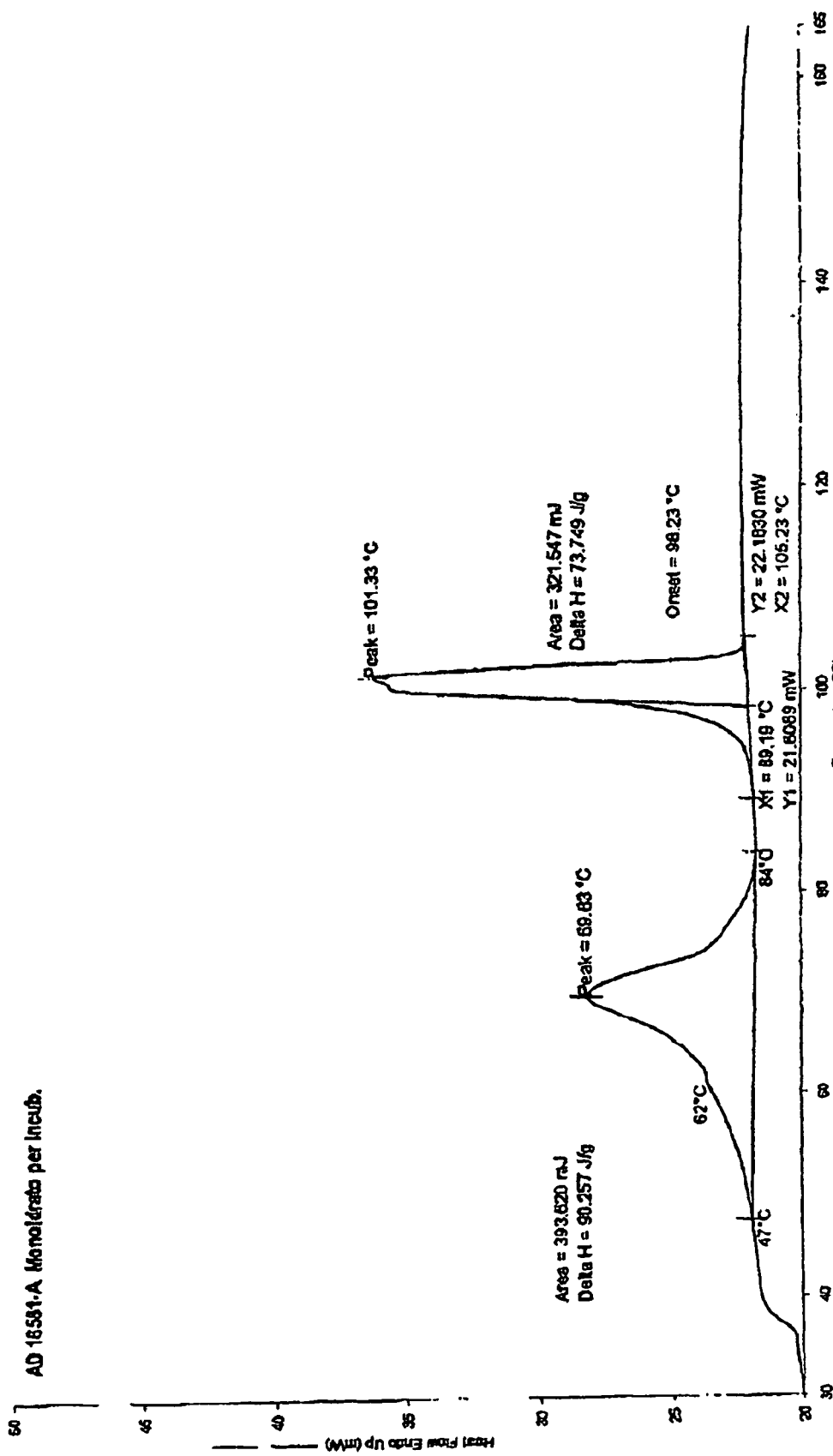

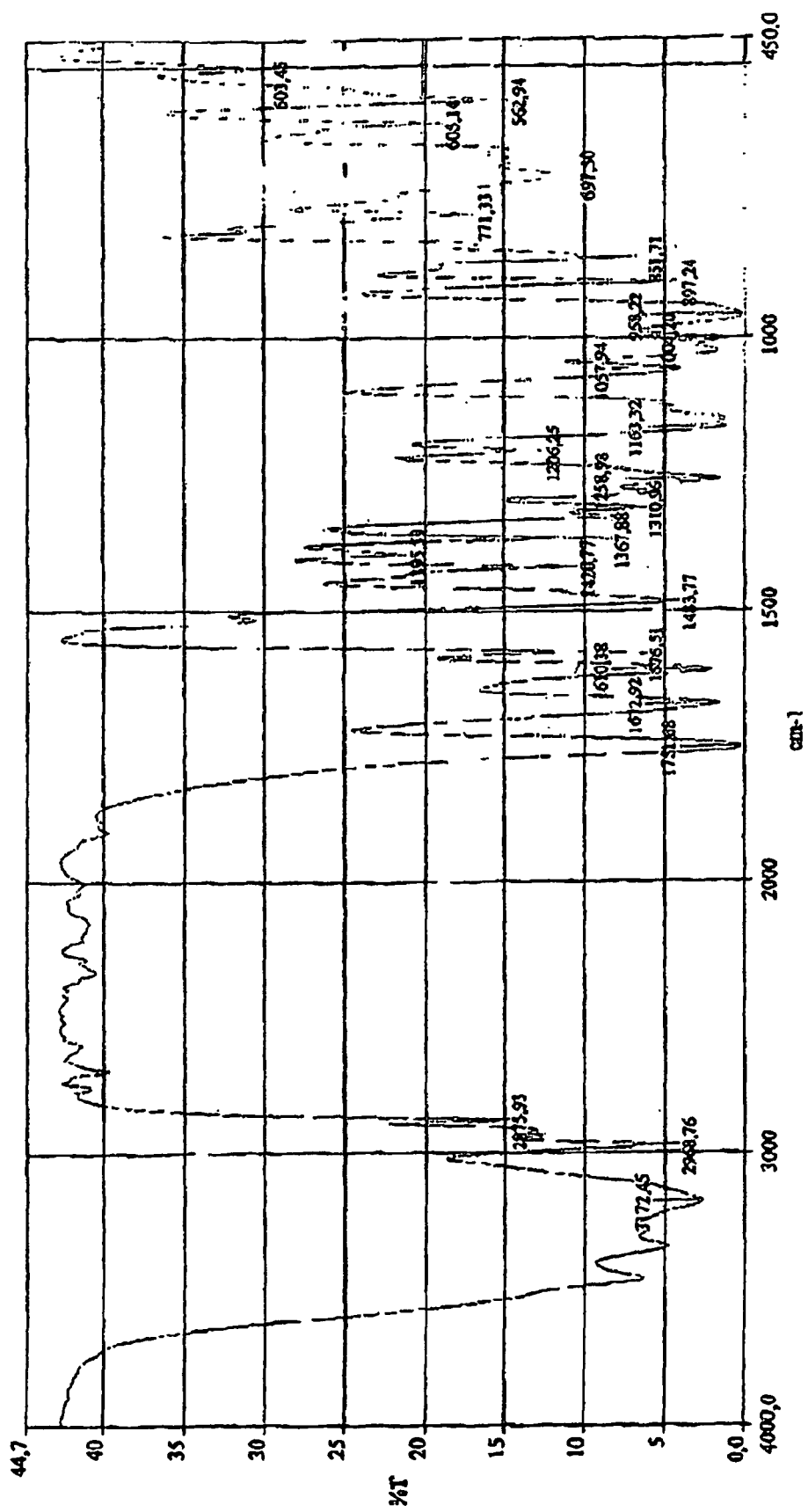

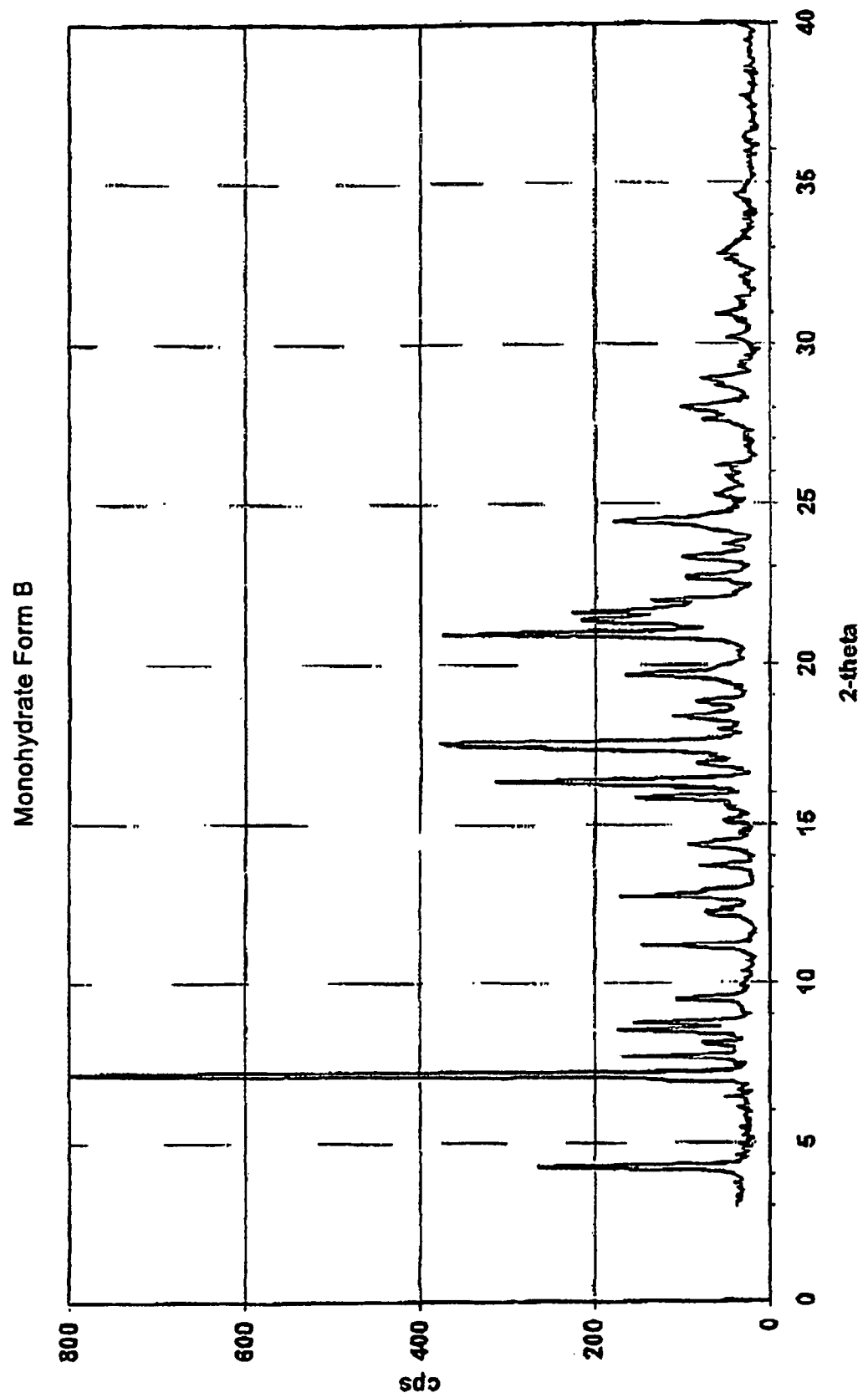
Figure 12 - X ray

ADEFOVIR DIPIVOXIL CRYSTALLINE MONOHYDRATE FORM

CROSS REFERENCE TO RELATED APPLICATION

This application is a 35 U.S.C. 371 National Phase Entry Application from PCT/EP2008/006320, filed Jul. 31, 2008, which claims the benefit of Italian Patent Application No. MI 2007A1594 filed on Aug. 2, 2007, the disclosure of which is incorporated herein in its entirety by reference.

The present invention relates to a novel Adefovir Dipivoxil crystalline monohydrate form, a process for its preparation and pharmaceutical compositions containing said monohydrate form.

TECHNOLOGICAL BACKGROUND

Adefovir Dipivoxil is a known nucleotide reverse transcriptase inhibitor used in clinic for the treatment of retrovirus infections, in particular HIV and HBV infections (U.S. Pat. No. 5,663,159).

WO 99/04774 and U.S. Pat. No. 6,451,340 disclose Adefovir crystalline forms, and particularly the crystalline form 1 (anhydrous) and the crystalline form 2 (dihydrate KF=6.7%).

The two crystalline forms were prepared and characterized. The analysis of form 1 is reported in FIGS. 1-3 whereas the analysis of form 2 is reported in FIGS. 4-6.

WO 00/35460 discloses pharmaceutical formulations comprising anhydrous and dihydrate Adefovir Dipivoxil and an alkali excipient.

DISCLOSURE OF THE INVENTION

A novel Adefovir Dipivoxil crystalline monohydrate form has now been found, which is pharmaceutically advantageous over the known amorphous and crystalline forms.

The monohydrate form object of the invention has a water content measured according to Karl Fischer ranging from 3% to 5% and DSC analysis, IR and X ray spectra as reported in FIGS. 7-9.

The invention also relates to pharmaceutical formulations containing the novel Adefovir Dipivoxil crystalline monohydrate form.

The novel form object of the invention is obtained by spontaneous evaporation of the crystallization solvent under controlled conditions. Said evaporation can be carried out either under reduced pressure or leaving the product at a room temperature of 20-25° C. for at least 24 hours, under room humidity conditions or under saturated humid atmosphere.

The invention is described in greater detail in the following examples.

EXAMPLE 1

25 g of Adefovir dipivoxil, prepared according to methods described in literature (e.g. following U.S. Pat. No. 5,663,159, Example 9) are dissolved in 70 ml of methylene chloride and 1 ml of methanol.

A chromatographic column is packed with 12 g of silica. The product solution is loaded on the column and eluted with a further 600 ml of methylene chloride.

By spontaneous evaporation of the solvent at room temperature and humidity for at least 24 hrs, or by spontaneous evaporation of the solvent at 25° C. under saturated humid atmosphere for 24 hrs, 25 g of Adefovir dipivoxil are obtained having KF from 3% to 5% and which is found to be a monohydrate (form A).

DSC analysis, IR and X ray spectra of the monohydrate are reported in FIGS. 7-9. By way of comparison, the corresponding DSC, IR, and X ray spectra of the anhydrous and dihydrate forms, prepared as described in WO 99/04774 and U.S. Pat. No. 6,451,340, are also reported in FIGS. 1-6.

EXAMPLE 2

25 g of Adefovir dipivoxil, prepared according to methods described in literature (e.g. following U.S. Pat. No. 5,663,159, Example 9) are dissolved in 70 ml of methylene chloride and 1 ml of methanol.

A chromatographic column is packed with 12 g of silica. The product solution is loaded on the column and eluted with a further 600 ml of methylene chloride.

The product obtained by evaporation to dryness of the solvent in vacuo, is kept in humid atmosphere for 24 hrs, to obtain 25 g of Adefovir dipivoxil having KF from 3% to 5% and which is found to be a monohydrate (form B).

DSC analysis, IR and X ray spectra of the monohydrate (form B) are reported in FIGS. 10-12.

BRIEF DESCRIPTION OF THE DRAWINGS

FIG. 1 shows a thermogram obtained by differential scanning calorimetry (DSC) of form 1-anhydrous crystals.

FIG. 2 shows an infrared absorption spectrum (IR) for form 1-anhydrous crystals.

FIG. 3 shows a form 1-anhydrous crystal x-ray spectra pattern. FIG. 4 shows a thermogram obtained by differential scanning calorimetry (DSC) of form 2-dihydrate crystals.

FIG. 5 shows an infrared absorption spectrum (IR) for form 2-dihydrate crystals.

FIG. 6 shows a form 2-dihydrate crystal x-ray spectra pattern.

FIG. 7 shows a thermogram obtained by differential scanning calorimetry (DSC) of monohydrate crystals—form A.

FIG. 8 shows an infrared absorption spectrum (IR) for monohydrate crystals—form A.

FIG. 9 shows a monohydrate crystal—form A x-ray spectra pattern.

FIG. 10 shows a thermogram obtained by differential scanning calorimetry (DSC) of monohydrate crystals—form B.

FIG. 11 shows an infrared absorption spectrum (IR) for monohydrate crystal—form B.

FIG. 12 shows a monohydrate crystal—form B x-ray spectra pattern.

The invention claimed is:

1. Crystalline monohydrate Adefovir Dipivoxil.

2. The crystalline monohydrate Adefovir Dipivoxil according to claim 1, wherein said crystalline monohydrate Adefovir Dipivoxil has a water content ranging from 3% to 5% as measured using the Karl Fischer method and a DSC analysis as shown in FIG. 7 or 10.

3. A pharmaceutical composition comprising crystalline monohydrate Adefovir Dipivoxil according to claim 1 in combination with a pharmaceutically acceptable carrier.

4. A pharmaceutical composition comprising crystalline monohydrate Adefovir Dipivoxil according to claim 2 in combination with a pharmaceutically acceptable carrier.

* * * * *